US00PP13093P2

(12) United States Plant Patent
Vandenberg

(10) Patent No.: US PP13,093 P2
(45) Date of Patent: Oct. 15, 2002

(54) CHRYSANTHEMUM PLANT NAMED 'FALL CONCERTO'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 1 days.

(21) Appl. No.: 09/837,585

(22) Filed: Apr. 19, 2001

(51) Int. Cl.[7] ..... A01H 5/00
(52) U.S. Cl. ..... Plt./290
(58) Field of Search ..... Plt./289, 290, 287

(56) References Cited

U.S. PATENT DOCUMENTS 4,616,099 * 10/1986 Sparkes ..... 47/58

OTHER PUBLICATIONS

Shukla, et al., 1993, "Mutation studies on early and late varieties of garden chrysanthemums", J. Nuclear Agric. Biol., 22 (3–4): 138–142.*

Broertjes, et al., 1980, "A mutant of a mutant of a . . . Irradiation of progressive radiation induced mutants in a mutation breeding programme with *Chrysanthemum morifolium*", Euphytica, 29:525–530.*

Gosling, ed., 1979, "The Chrysanthemum Manual—6$^{th}$ edition", The National Chrysanthemum Society, London, Essex Telegraph Press, Ltd., pp. 329–336.*

Broertjes et al., 1978, "Application of Mutation Breeding Methods in the Improvement of Vegetatively Propagated Crops", Elsevier Sci. Pub Co., New York, pp. 162–175.*

Searle, et al., 1968, "Chrysanthemums The Year Round", Blanford Press, London, pp. 27–29, 320–327.*

Chan, 1966, "Chrysanthemum and rose mutations induced by x–rays", Am. Soc. Hort. Sci. Proc., pp. 613–620.*

Broertjes, 1966, "Mutation breeding of chrysanthemums", Euphytica, 15:156–162.*

Dowrick, et al., 1966, "The induction of mutations in chrysanthemum using x– and gamma radiation", Euphytica, 15:204–210.*

* cited by examiner

*Primary Examiner*—Howard J. Locker
(74) *Attorney, Agent, or Firm*—C. A. Whealy

(57) ABSTRACT

A distinct cultivar of Chrysanthemum plant named 'Fall Concerto', characterized by its upright plant habit; freely branching growth habit; uniform and freely flowering habit; decorative-type inflorescences; and golden bronze ray florets.

1 Drawing Sheet

BACKGROUND OF THE INVENTION

The present invention relates to a new and distinct cultivar of Chrysanthemum plant, botanically known as *Chrysanthemum×morifolium* and hereinafter referred to by the name 'Fall Concerto'.

The new cultivar is a product of a planned breeding program conducted by the Inventor in Salinas, Calif. and Fort Myers, Fla. The objective of the breeding program is to create new garden-type Chrysanthemum cultivars having inflorescences with desirable inflorescence forms, attractive floret colors and good garden performance.

The new Chrysanthemum is a naturally-occurring whole plant mutation of a proprietary induced mutation that originated by exposing unrooted cuttings of the Chrysanthemum cultivar Empire Concerto, disclosed in U.S. Plant Pat. No. 11,827, to X-ray radiation in March, 1997, in Fort Myers, Fla. The new Chrysanthemum was discovered and selected by the Inventor as a single flowering plant within a population of flowering plants of the irradiated selection in October, 1997 in a controlled environment in Salinas, Calif. The selection of this plant was based on its desirable inflorescence form, attractive ray floret color and good garden performance.

Asexual reproduction of the new cultivar by terminal cuttings taken in a controlled environment in Salinas, Calif.

since December, 1997, has shown that the unique features of this new Chrysanthemum are stable and reproduced true to type in successive generations.

SUMMARY OF THE INVENTION

The cultivar Fall Concerto has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Fall Concerto'. These characteristics in combination distinguish 'Fall Concerto' as a new and distinct cultivar:

1. Upright plant habit.
2. Freely branching, dense, full plants.
3. Uniform and freely flowering.
4. Decorative-type inflorescences.
5. Golden bronze-colored ray florets.

Compared to plants of the cultivar Empire Concerto, plants of the new Chrysanthemum are more mounding, flower slightly later and differ in ray floret color.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Fall Concerto'.

The photograph at the bottom of the sheet comprises a close-up view of typical inflorescences of the cultivar 'Fall Concerto'.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., under conditions which approximate those generally used in commercial garden Chrysanthemum production. One rooted cutting was planted in a 15-cm container in July, 2000 and plants were grown under natural season conditions. Plants were not pinched, that is, the terminal apex was not removed to enhance branching. Measurements and numerical values represent averages for typical flowering plants.

Botanical classification: *Chrysanthemum×morifolium* cultivar Fall Concerto.

Commercial classification: Decorative-type garden Chrysanthemum.

Parentage: Naturally-occurring whole plant mutation of a proprietary *Chrysanthemum×morifolium* induced mutation, not patented.

Propagation:

*Type*.—Terminal tip cuttings.

*Time to initiate roots*.—About four days at 21° C.

*Time to produce a rooted cutting*.—About ten days at 21° C.

*Root description*.—White, fine and fibrous.

*Rooting habit*.—Freely branching.

Plant description:

*Appearance*.—Perennial herbaceous decorative-type garden Chrysanthemum. Inverted triangle; upright plant form. Stems initially upright, then slightly outwardly spreading giving a uniformly mounded appearance to the plant. Freely branching with about 9 lateral branches per plant.

*Plant height*.—About 31 cm.

*Plant diameter*.—About 29 cm.

*Lateral branches*.—Length: About 26 cm. Diameter: About 5 mm. Internode length: About 1.9 cm. Aspect: Mostly upright. Texture: Pubescent. Color: 144A, heavily overlain with anthocyanin, close to 187A.

*Foliage description*.—Leaf arrangement: Alternate. Length: About 4.6 cm. Width: About 3.7 cm. Apex: Cuspidate to mucronate. Base: Attenuate to truncate. Margin: Palmately lobed, sinuses parallel to divergent. Texture: Both surfaces, pubescent; veins prominent on lower surface. Color: Young foliage upper surface: 147A. Young foliage lower surface: Close to 147B. Mature foliage upper surface: 147A. Mature foliage lower surface: 147B. Venation upper surface: 147A to 147B. Venation lower surface: 147B. Petiole length: About 1.7 cm. Petiole diameter: About 2 mm. Petiole color, both surfaces: Close to 146C.

Inflorescence description:

*Appearance*.—Decorative-type inflorescence form with elongated oblong-shaped ray florets. Inflorescences borne on terminals above foliage, arising from leaf axils. Disk and ray florets arranged acropetally on a capitulum. About 7 inflorescences per lateral; about 63 inflorescences per plant.

*Flowering response*.—Under natural season conditions, plants flower in early October in the Northern Hemisphere and continue to flower for at least three weeks depending on weather conditions.

*Inflorescence bud (before showing color)*.—Height: About 6 mm. Diameter: About 8 mm. Phyllary color: Close to 143A.

*Inflorescence size*.—Diameter: About 5.4 cm. Depth (height): About 1.5 cm. Disc diameter: About 3 mm or less, inconspicuous. Receptacle diameter: About 5 mm.

*Ray florets*.—Shape: Elongated oblong to somewhat spatulate. Length: About 2.6 cm. Corolla tube length: About 1.5 cm. Width: About 7 mm. Apex: Acute, emarginate or dentate. Margin: Entire. Texture: Smooth, glabrous, satiny. Orientation: Initially upright and incurved, then perpendicular to the peduncle and concave. Number of ray florets per inflorescence: About 174. Color: When opening, upper and lower surfaces: 12A to 14A overlain with faint 45A to 46A; margins and towards apices, 45A to 46A; overall tonality, more red than 163A. Opened inflorescence, upper surface: 12A overlain with very faint 45A to 46A; margins and towards apices, 45A to 46A; overall tonality, slightly more red than 12A; fading to 12A with little or no red at margins and towards apices. Opened inflorescence, lower surface: 12A to 12B.

*Disc florets*.—Shape: Tubular, apex dentate. Length: About 6 mm. Width: Apex: About 2 mm. Base: About 1 mm. Number of disc florets per inflorescence: Less than 20. Color: Immature: Apex: Close to 46A. Mid-section: 9A. Base: 155D. Mature: Apex: 9A. Mid-section: 154D. Base: 155D.

*Peduncle*.—Aspect: Flexible, angled about 35° from the stem. Length: First peduncle: About 6.7 cm. Fourth peduncle: About 9 cm. Diameter: About 2.5 mm. Texture: Pubescent. Color: Close to 187A.

*Reproductive organs*.—Androecium: Present on disc florets only. Anther color: 9A. Pollen: Moderate. Pollen color: 15A. Gynoecium: Present on both ray and disc florets.

*Seed*.—Seed production has not been observed.

Disease resistance: Plants of the new Chrysanthemum have not been shown to be resistant to pathogens common to Chrysanthemums.

Garden performance: Plants of the new Chrysanthemum have been observed to be tolerant to rain and wind.

It is claimed:

1. A new and distinct cultivar of Chrysanthemum plant named 'Fall Concerto', as illustrated and described.

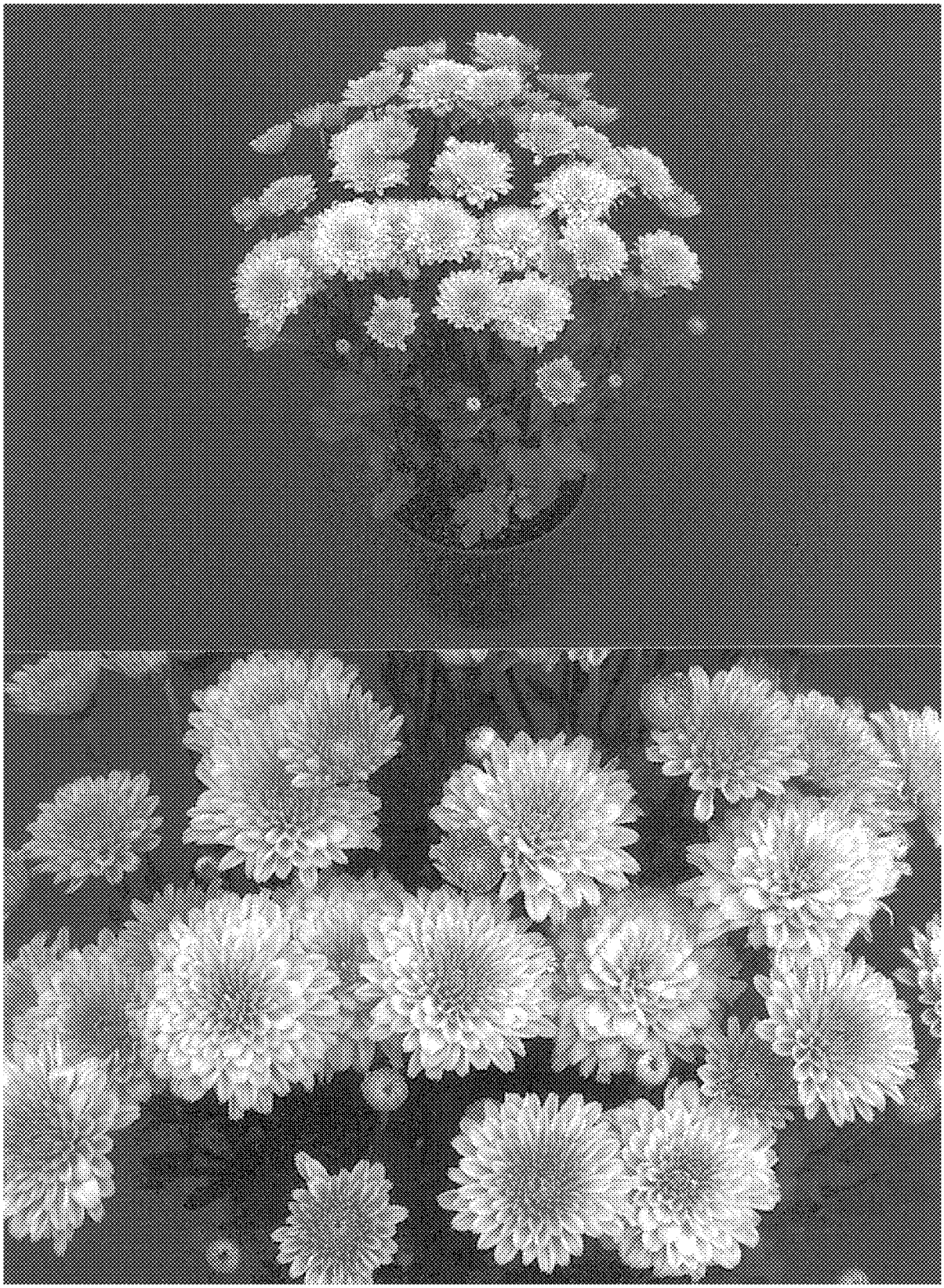

* * * * *